Feb. 23, 1960 F. MEILLAND Plant Pat. 1,912
ROSE PLANT
Filed Jan. 8, 1959
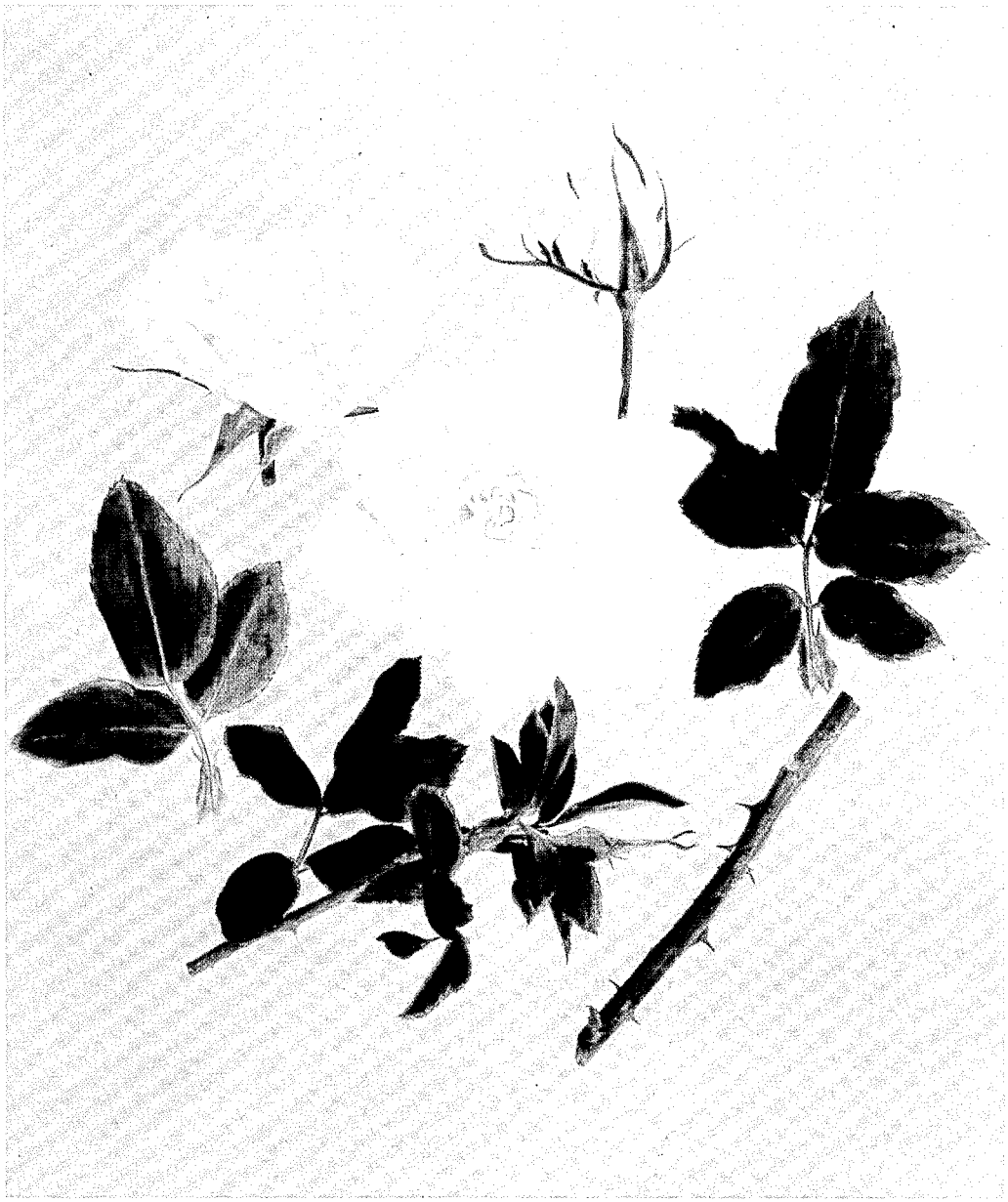
Inventor.
Francis Meilland, Deceased
By: Marie Louise Meilland, née Paolino
Legal Representative
By: Robb & Robb
Attorneys United States Patent Office Plant Pat. 1,912
Patented Feb. 23, 1960

1,912

ROSE PLANT

Francis Meilland, deceased, late of Cap d'Antibes, France, by Marie Louise Meilland, nee Paolino, legal representative, Cap d'Antibes, France Application January 8, 1959, Serial No. 785,768

1 Claim. (Cl. 47—61)

The present invention relates to a new and distinct variety of rose plant of the grandiflora class, which was originated by the deceased by crossing an unnamed and unpatented seedling of "Joanna Hill" (unpatented) × "Eclipse" (Plant Patent No. 172) with the variety "Michelle Meilland" (unpatented).

The primary objective of this breeding was to develop a new rose variety combining the excellent bloom form and free blooming habit of the unnamed seedling parent with the vigor and habit of growth of the parent "Michelle Meilland" (a seedling of "Joanna Hill" × "Peace," Plant Patent No. 591), while maintaining and strengthening the desirable inheritable characteristics of the common grandparent "Joanna Hill." These objectives were fully achieved, along with other desirable improvements, as evidenced by the following unique combination of characteristics which are outstanding in the new variety and distinguish it from its parents as well as from all other varieties of which the deceased was aware:

(1) An extra vigorous and well-balanced grandiflora habit of growth;

(2) A well clothed and decorative effect of the clean-cut, medium sized, light green foliage;

(3) Exceptionally good floriferousness which is superior to that of any of the commonly known yellow rose varieties, with each flower borne on a stem of suitable cutting length, whether borne singly or in candelabra-type clusters;

(4) Full, high-centered blooms that are more double and full than those of "Eclipse," and which open from a bud form somewhat similar to that of "Eclipse"; and (5) An Aureolin Yellow general color tonality of the flowers, with their petals tinted with Mimosa Yellow at the otuer edges.

Asexual reproduction of the new variety by budding and grafting, as performed in France and also at West Grove, Pennsylvania, U.S.A., shows that the foregoing characteristics and distinctions come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of the new variety, with color terminology in accordance with the Horticultural Colour Chart of the British Colour Council, except where general color terms of ordinary dictionary significance are obvious:

Type: Hardy; bush; outdoor; seedling; for cut flowers and for garden decoration.

Class: Grandiflora.

Breeding: Seedling.

*Seed parent.*—An unnamed seedling of "Joanna Hill" × "Eclipse."

*Pollen parent.*—"Michelle Meilland."

Propagation: Holds its distinguishing characteristics through succeeding propagations by budding and grafting.

*Flower*

Locality where grown and observed: West Grove, Pennsylvania, U.S.A.

Flowers borne: Usually singly to stem, but sometimes two, three or four to stem; in irregular candelabra clusters; each flower in cluster borne on short to medium cutting stem bearing foliage; on strong stems of medium length.

Quantity of bloom: Abundant, outdoors.

Continuity: Continuous.

Fragrance: Moderate. Nature—tea.

Bud:

*Peduncle.*—Medium length; medium caliper; stiff; rough; with numerous red hairs. Color—Fern Green, Plate 0862/2, overlaid with Indian Lake, Plate 826.

*Before calyx breaks.* — Size — medium. Form—pointed-ovoid; with a conspicuous neck; with foliaceous appendages on the surface of the bud; with much-cut foliaceous parts extending beyond the tip of the bud equal to ¾ or more of its length.

*As calyx breaks.*—Color—Citron Green, Plate 763/2, dotted and lightly washed with Rose Opal, Plate 022/1.

*As first petal opens.*—Size—from medium to large. Form—pointed-ovoid. Color: outside—Empire Yellow, Plate 603, washed with Citron Green, Plate 763/1 in area adjoining the midrib; inside—Aureolin, Plate 3, veined and marked by underlying areas of Lettuce Green, Plate 861/2.

*Opening.*—Opens up well.

Bloom:

*Size (when fully open).*—Medium; from 4 inches to 4½ inches.

*Petalage.*—Very double; from 40 to 45 petals; arranged regularly.

*Form.*—High-centered at first, but becoming cupped; petals at first being very loosely rolled outward, and remaining very loosely rolled outward at maturity.

Petals: Medium thickness; with inside satiny and outside shiny. Shape: outer—obovate, with generally no notches; intermediate—obovate, with generally no notches; inner—obovate, with no notches.

This description of a newly opened flower was made from a rose grown outdoors in the month of September at West Grove, Pennsylvania, U.S.A.:

*Color.*—Outer petal: outside surface—upper half of petal Primrose Yellow, Plate 601/3, with lower half Lemon Yellow, Plate 4/1, veins of which color pass into the upper half of the petal; inside surface—upper half of petal a tint of Primrose Yellow, slightly lighter than Plate 601/3, with basal half Lemon Yellow, Plate 4, veins of which color radiate into the upper half of the petal. Intermediate petal: outside surface—a tint of Primrose Yellow slightly lighter than Plate 601/3 at apex, shading to Mimosa Yellow, Plate 602/2, with lower half of petal Aureolin, Plate 3/1, veined with Aureolin, Plate 3; inside surface—apex a tint of Primrose Yellow slightly lighter than Plate 601/3, shading to Mimosa Yellow, Plate 602/2 and then to Aureolin, Plate 3. Inner petal: outside surface—Aureolin, Plate 3/1, with base and point of attachment Aureolin, Plate 3; inside surface—Aureolin, Plate 3/1 at upper edge, shading to Aureolin, Plate 3.

This description was made from a rose that was open for 3 days outdoors in the month of September at West Grove, Pennsylvania, U.S.A.:

*Color.*—Outer petal: outside surface—Primrose Yellow, Plate 601/3, shading to Mimosa Yellow, Plate 602/1 and to Empire Yellow, Plate 603 at base; inside surface—Primrose Yellow, Plate 601/3, shading to Sulphur Yellow, Plate 1/2 and to Aureolin, Plate 3/1 at base of petal, with larger part of petal showing veins of Aureolin, Plate 3/1. Inner petal: outside surface—Mimosa Yellow, Plate 601/2 over upper half of petal, shading to Empire Yellow, Plate 603 at base; inside surface—Primrose Yellow, Plate 601/2 at apex, shading to Sulphur Yellow, Plate 1/2 and to Aureolin, Plate 3/1 at base.

*General color effect.*—Newly opened flower—Aureolin, Plate 3 at center, with outer petals showing Mimosa Yellow, Plate 602/2. 3-days open—Aureolin, Plate 3 at center, with outer petals Primrose Yellow, Plate 601/2.

*Behavior.*—Drop off cleanly.

*Flower longevity.*—On bush in garden—4 days in September. Cut roses grown outdoors and kept at living-room temperatures—5 days in September.

*Reproductive organs*

Stamens: Medium number; arranged regularly about pistils.

Filaments: Many; most with anthers; medium length. Color—Aureolin, Plate 3.

Anthers: All open at once; medium size; seldom an anther fused with a petaloid. Color—Buttercup Yellow, Plate 5.

Pollen: Moderate abundance. Color—gold.

Pistils: Medium number.

Styles: Uneven; medium length; medium heavy; bunched.

Stigma: Color—upper half of style—red; lower half of style—yellow.

Ovaries: Some protruding from receptacle.

Hips: None observed.

Sepals: Permanent; long; spear-shaped.

Seeds: None observed.

*Plant*

Foliage:

*Leaves.*—Some compound of 7 leaflets, and some compound of 3 and 5 leaflets; abundant; medium size; leathery.

*Leaflets.*—Shape—narrowly ovoid, with apex acute. Base—acute. Margin—simply serrate.

*Color.*—Mature: upper surface—Parsley Green, Plate 00962; under surface—Sage Green, Plate 000861/1. Young: upper surface—Fern Green, Plate 0862, overlaid with Pansy Purple, Plate 928; under surface—Lavender Green, Plate 000761, overlaid with Erythrite Red, Plate 0027.

*Rachis (the supporting stem of the compound leaf).*—Medium caliper. Upper side—grooved; hairy. Under side—sparsely prickly.

*Stipules.*—Moderately long; medium width; with short points turning out at an angle of more than 45°.

*Disease resistance.*—Comparable to that of the average variety grown under the same cultural conditions at West Grove, Pennsylvania, U.S.A.

Growth:

*Habit.*—Bushy; upright; much-branched.

*Growth.*—Vigorous.

*Canes.*—Medium caliper.

*Main stem.*—Bright. Color—slightly darker than Lettuce Green, Plate 816. Prickles—several; color—Fern Green, Plate 0862. Hairs—none.

*Branches.*—Bright. Color—Lettuce Green, Plate 861. Prickles—several; color—Fern Green, Plate 0862. Hairs—none.

*New shoots.*—Dull. Color—Fern Green, Plate 0862/1, overlaid with Oxblood Red, Plate 00823. Prickles—several; color—Oxblood Red, Plate 00823. Hairs—none.

What is claimed is:

A new and distinct variety of rose plant of the grandiflora class, substantially as herein shown and described, characterized particularly as to novelty by the unique combination of an extra vigorous and well-balanced grandiflora habit of growth, well-clothed and decorative effect of the clean-cut, medium sized, light green foliage, exceptionally good floriferousness, with each flower borne on a stem of suitable cutting length irrespective of whether the flowers are borne singly or in candelabra-type clusters, full, high-centered double blooms which open from a bud form somewhat similar to that of the variety "Eclipse" (Plant Patent No. 172), and an Aureolin Yellow general color tonality of the flowers, with the flower petals tinted a Mimosa Yellow at their outer edges.

No references cited.